United States Patent
Hingston et al.

(10) Patent No.: US 10,507,128 B2
(45) Date of Patent: Dec. 17, 2019

(54) DEVICES AND METHODS FOR REDUCING ABSORPTION

(71) Applicants: Boston Scientific Scimed, Inc., Maple Grove, MN (US); Lifespan Corporation, Providence, RI (US)

(72) Inventors: John A. Hingston, Framingham, MA (US); Gene T. Storbeck, Franklin, MA (US); Jeri Ann Hiller, Westford, MA (US); Kathleen Corcoran, Watertown, MA (US); Kali L. Manning, Providence, RI (US); Selina M. Merkling, St. Louis Park, MN (US); Gary Dean Roye, Cranston, RI (US); Sivamainthan Vithiananthan, Sharon, MA (US); Beth Ryder, Warwick, RI (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 387 days.

(21) Appl. No.: 15/352,797

(22) Filed: Nov. 16, 2016

(65) Prior Publication Data
US 2017/0135836 A1    May 18, 2017

Related U.S. Application Data

(60) Provisional application No. 62/256,380, filed on Nov. 17, 2015.

(51) Int. Cl.
*A61F 2/04* (2013.01)
*A61F 5/00* (2006.01)

(52) U.S. Cl.
CPC .................. *A61F 5/0076* (2013.01)

(58) Field of Classification Search
CPC ............... A61F 5/0076; A61F 5/0079
See application file for complete search history.

(56) References Cited

U.S. PATENT DOCUMENTS

| | | | |
|---|---|---|---|
| 4,315,509 A * | 2/1982 | Smit | A61F 5/0076 417/474 |
| 5,306,300 A | 4/1994 | Berry | |
| 5,820,584 A * | 10/1998 | Crabb | A61F 2/04 604/500 |
| 7,037,344 B2 | 5/2006 | Kagan et al. | |
| 7,122,058 B2 | 10/2006 | Levine et al. | |
| 7,789,848 B2 | 9/2010 | Gannoe et al. | |
| 8,882,698 B2 | 11/2014 | Levine et al. | |
| 10,172,735 B2 * | 1/2019 | McGuckin, Jr. | A61F 5/0076 |
| 2004/0092892 A1 * | 5/2004 | Kagan | A61F 2/04 604/264 |
| 2005/0085787 A1 * | 4/2005 | Laufer | A61B 17/1114 604/500 |
| 2005/0125075 A1 * | 6/2005 | Meade | A61B 17/0401 623/23.64 |
| 2007/0233162 A1 * | 10/2007 | Gannoe | A61B 17/072 606/153 |
| 2007/0282452 A1 * | 12/2007 | Weitzner | A61F 2/04 623/23.7 |

(Continued)

*Primary Examiner* — Susan S Su
(74) *Attorney, Agent, or Firm* — Bookoff McAndrews, PLLC (57) ABSTRACT

A reduced absorption device may include a proximal anchor and a distal sleeve including a frame and a membrane. The membrane may include a plurality of porous regions, and each porous region may be configured to align with a corresponding region of an intestine configured to absorb nutrients.

17 Claims, 5 Drawing Sheets

(56) References Cited

U.S. PATENT DOCUMENTS

| | | | | |
|---|---|---|---|---|
| 2007/0282453 A1* | 12/2007 | Weitzner | A61F 2/04 | 623/23.7 |
| 2008/0195226 A1* | 8/2008 | Williams | A61F 2/04 | 623/23.67 |
| 2009/0062717 A1* | 3/2009 | Laufer | A61F 5/0076 | 604/8 |
| 2009/0187206 A1* | 7/2009 | Binmoeller | A61F 5/0036 | 606/191 |
| 2010/0191167 A1* | 7/2010 | Laufer | A61F 5/0076 | 604/8 |
| 2011/0172585 A1* | 7/2011 | Weitzner | A61F 2/04 | 604/8 |
| 2012/0116285 A1* | 5/2012 | Duggirala | A61F 5/0079 | 604/8 |
| 2012/0184893 A1* | 7/2012 | Thompson | A61F 2/04 | 604/9 |
| 2013/0324926 A1* | 12/2013 | Nelson | A61F 2/04 | 604/115 |
| 2014/0276337 A1* | 9/2014 | Reo | A61F 5/0076 | 604/8 |
| 2014/0350694 A1* | 11/2014 | Behan | A61F 2/04 | 623/23.65 |
| 2015/0065938 A1* | 3/2015 | Zeiner | A61F 5/0076 | 604/8 |
| 2015/0065939 A1* | 3/2015 | Harris | A61F 5/0089 | 604/8 |
| 2015/0282971 A1* | 10/2015 | McGuckin, Jr. | A61F 5/0076 | 623/23.69 |
| 2016/0058803 A1* | 3/2016 | Bangera | A61K 9/7023 | 424/423 |
| 2016/0058914 A1* | 3/2016 | Bangera | A61K 35/74 | 623/23.67 |
| 2017/0027729 A1* | 2/2017 | Abu Dayyeh | A61F 5/0036 | |
| 2018/0110641 A1* | 4/2018 | Storbeck | A61F 5/0079 | |

* cited by examiner

DEVICES AND METHODS FOR REDUCING ABSORPTION

CROSS-REFERENCE TO RELATED APPLICATION

This application claims the benefit of priority under 35 U.S.C. § 119 to U.S. Provisional Patent Application No. 62/256,380, filed Nov. 17, 2015, the entirety of which is incorporated herein by reference.

TECHNICAL FIELD

Examples of the present disclosure relate generally to devices and related methods for reducing absorption of food in the gastrointestinal tract of a patient.

BACKGROUND

Current implantable devices for obesity treatment may prevent food from contacting portions of the gastrointestinal system. For example, intestinal sleeves may prevent chyme from contacting a portion of the intestine. While existing devices may potentially enable weight loss due to reduced calorie absorption through the intestine, they may cause malnutrition by blocking portions of the intestine that absorb nutrients.

SUMMARY

Examples of the present disclosure relate to, among other things, devices and methods for reducing the absorption of food in the gastrointestinal system. Each of the examples disclosed herein may include one or more of the features described in connection with any of the other disclosed examples.

In one example, a reduced absorption device may include a proximal anchor and a distal sleeve including a frame and a membrane. The membrane may include a plurality of porous regions, and each porous region may be configured to align with a corresponding region of an intestine configured to absorb nutrients.

Additionally or alternatively, any of the devices described herein may include one or more of the following features: the membrane may include a plurality of weakened regions, with at least one weakened region being configured to allow the anchor to separate from at least a portion of the sleeve; the anchor may include a self-expandable frame; the anchor may include a plurality of circumferential loops and a plurality of connectors extending between the circumferential loops, and the connectors may extend radially outward relative to the circumferential loops; the anchor may include a plurality of attachments configured to secure the anchor to the intestine; the sleeve may include at least three porous regions, wherein a first porous region may be configured to align with a first region of the intestine configured to absorb nutrients, a second porous region may be configured to align with a second region of the intestine, the second region of the intestine being distal to the first region of the intestine and being configured to absorb water soluble vitamins, and a third porous region may be configured to align with a third region of the intestine, the third region of the intestine being distal to the second region of the intestine and being configured to absorb fat soluble vitamins; the sleeve may include at least five porous regions, wherein a first porous region may be configured to align with a first region of the intestine that absorbs $Fe^{++}$, $Ca^{++}$, and $Mg^{++}$, a second porous region may be configured to align with second region of the intestine that produces GIP and CCK, a third porous region may be configured to align with third region of the intestine that absorbs water soluble vitamins, a fourth porous region may be configured to align with a fourth region of the intestine that produces GLP-1, oxyntomodulin, and PYY, and a fifth porous region may be configured to align with a fifth region of the intestine that absorbs fat soluble vitamins; each porous region may be separated from an adjacent porous region by an impermeable region; at least one porous region may differ from at least one other porous region by at least one of a) total number of pores, b) the size of individual pores, or c) the arrangement of pores; the pores of at least one porous region may be configured to allow tissue ingrowth; an interior of the sleeve may be coated with a material that is a lower friction material than a material of the sleeve; at least one of the anchor, the frame of the sleeve, or the membrane of the sleeve may be bioabsorbable; the sleeve may include a weakened region in a spiral configuration around the sleeve, and the sleeve may be configured to separate along the weakened region; the anchor and the sleeve may be modular components configured to be at least one of separately implanted in the patient or separately removed from the patient; and the distal sleeve may be self-expandable.

In another example, a reduced absorption device may include a proximal bioabsorbable frame and a distal sleeve including a bioabsorbable frame and a bioabsorbable membrane. The membrane may include a plurality of porous regions, with each porous region being separated from an adjacent porous region by an impermeable region.

Additionally or alternatively, any device described herein may include one or more of the following features: the sleeve may include a weakened region in a spiral configuration around the sleeve, and the sleeve may be configured to separate along the weakened region; and the anchor and the sleeve may be modular components configured to be at least one of separately implanted in the patient or separately removed from the patient.

In another example, a method for reducing absorption in a patient may include positioning a reduced absorption device within an intestine of the patient, the reduced absorption device including a proximal anchor and a distal sleeve. The proximal anchor may be positioned distal to a pyloric sphincter, the sleeve may include a frame and a membrane, and the membrane may include a plurality of porous regions.

Additionally or alternatively, any method described herein may include one or more of the following steps or features: the distal sleeve may be self-expandable; positioning the reduced absorption device may include transorally introducing the device and passing the device through an esophagus and a stomach; the method may further include aligning a first porous region of the sleeve with a first region of the intestine configured to absorb nutrients, aligning a second porous region of the sleeve with a second region of the intestine, the second region of the intestine being distal to the first region of the intestine and being configured to absorb water soluble vitamins, and aligning a third porous region of the sleeve with a third region of the intestine, the third region of the intestine being distal to the second region of the intestine and being configured to absorb fat soluble vitamins; the method may further include aligning at least one porous region of the membrane with a region of the intestine configured to produce digestive hormones; and positioning the reduced absorption device may include positioning the anchor proximal to the duodenal papilla.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary examples of the present disclosure and together with the description, serve to explain the principles of the disclosure.

DETAILED DESCRIPTION

The present disclosure is drawn to devices and methods for reducing absorption of food in a patient's gastrointestinal system, particularly within the patient's intestine, while allowing the body to absorb certain nutrients from the food. As used herein, "food" may refer to any substance, whether solid or liquid, that is ingested or otherwise taken into the body. In one example, a reduced absorption device may include a proximal anchor and an elongated sleeve. The elongated sleeve may include pores that allow some contact between chyme and the intestinal wall. The pores may be configured to promote nutrient absorption without negating the weight loss benefits achieved by bypassing portions of the intestine.

Figure 1:
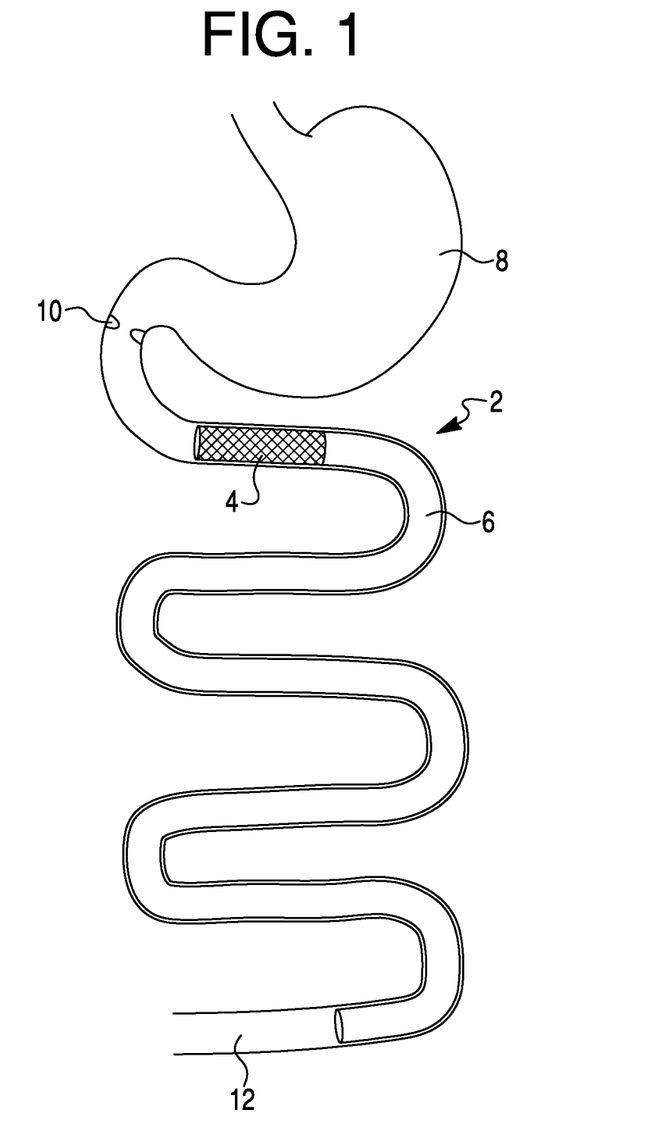
FIG. 1 illustrates a reduced absorption device implanted in the intestine.

Referring to FIG. 1, a reduced absorption device 2 may include a proximal anchor 4 and a distal sleeve 6. The device 2 may be positioned in an intestine 12 distal to the stomach 8 and distal to the pyloric sphincter 10. In various examples, the device 2 may have a length between 1-20 feet (0.3-6.1 meters), between 3-5 feet (0.9-1.5 meters), or about 2-4 feet (0.6-1.2 meters).

Figure 2:
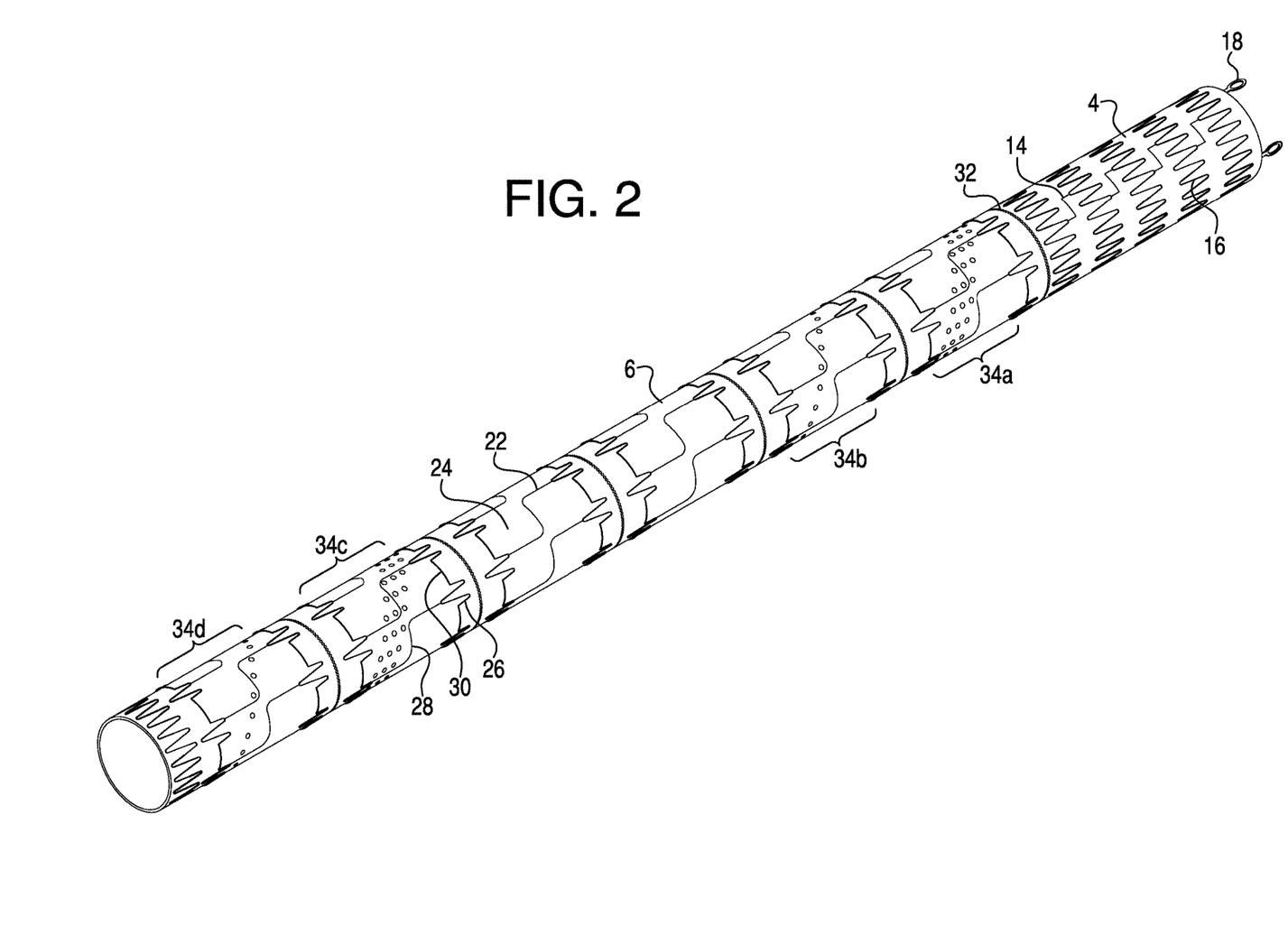
FIG. 2 illustrates a detailed view of a reduced absorption device.

Referring to FIG. 2, the anchor 4 may be similar to a stent. In one example, the anchor 4 may include a frame and a membrane covering the frame (e.g., a covered stent). In another example, the anchor 4 may include a bare frame without a membrane (e.g., a bare stent). The anchor 4 may include a laser cut nitinol frame that resists elongation or does not elongate. Alternatively, the anchor may include a braided design. The anchor 4 may be self-expandable, like nitinol stents. In an alternative example, the anchor 4 may be expanded by an expansion device, such as a balloon inserted within a lumen of anchor 4. Once implanted in a patient, the anchor 4 may exert a radially outward force to help secure the device 2 to the intestinal wall. In various examples, the anchor may have a length between 0.5-25 cm, 2-15 cm, or 3-8 cm.

The anchor 4 may include circumferential loops 16 and connectors 14 connecting the loops 16. The circumferential loops 16 may extend 360° around a circumference of the anchor 4 and may include a sinusoidal pattern. The connectors 14 may extend in a generally longitudinal direction and may connect adjacent loops 16. Each connector 14 may include one or more bends. The connectors 14 may extend radially outward relative to the circumferential loops 16 to help prevent migration of the anchor 4 and the device 2. To further secure the anchor 4 to the intestine, the anchor 4 may include attachments 18. The attachments 18 may be configured to receive a clip or tissue anchor secured to the intestinal wall, or may be configured to receive a suture used to suture the anchor 4 to the intestinal wall. The attachments 18 may allow a physician to grasp the device 2 with an appropriate tool, or by using sutures that have been passed through the attachments 18, to reposition the device 2 or to remove the device 2 from the patient. The attachments 18 may be used to secure device 2 to a delivery system or insertion catheter.

A sleeve 6 may be secured to a distal end of the anchor 4. The sleeve 6 may include a frame 22 and a membrane 24 (e.g., a coated stent). The membrane 24 may include silicone, liquid silicone rubber, polytetrafluoroethylene (PTFE), polyethylene terephthalate (PET), ultra-high-molecular-weight polyethylene (UHMWPE) or any biomaterial resistant to the stomach acid environment. In one example, the membrane 24 may cover the entire device 2, including the anchor 4, and may therefore be continuous with the membrane of the anchor 4. In one example, coating the device 2 with the membrane 24 may couple the sleeve 6 to the anchor 4. The frame 22 and membrane 24 may be integrally formed, with the membrane 24 molded around all of or portions of the frame 22. The frame 22, and therefore the sleeve 6, may be self-expandable. The frame 22 of the sleeve 6 may include a plurality of circumferential loops 26 and connectors 28 joining at least some of the circumferential loops 26. The circumferential loops 26 may extend 360° around a circumference of the sleeve 6. The circumferential loops 26 may include portions having a sinusoidal pattern and portions 30 connecting the sinusoidal portions, which may allow the device 2 to be compressed and expanded without longitudinal elongation. The connectors 28 may extend in a generally longitudinal direction and may connect adjacent loops 26. Each connector 28 may include one or more bends. The connectors 28 may extend radially outward relative to the loops 26 to help prevent migration of the sleeve 6. Furthermore, portions 30 of the circumferential loops 26 may extend radially outward from the remaining portions of the loops 26 to help prevent migration. The device 2, when implanted in a patient, may exert a radially outward force against the intestinal wall. In one example, when implanted, the radially outward force exerted by the sleeve 6 is less than the radially outward force exerted by the anchor 4.

The frame of the sleeve 6 or the anchor 4 may be any suitable material sufficient to give structural integrity to the sleeve 6 or the anchor 4. The material of the frames may be biocompatible. For example, the frames may be nitinol, stainless steel, permanent polymers like PET, etc.

In one example, the device 2 may be bioabsorbable, biodegradable, or bioresorbable. The frame of the device may be made with PLLA, PLA or PLGA, for example, and the coating of the device may be a thin layer or sheet of bioabsorbable, biodegradable, or bioresorbable material. The device 2 therefore may degrade after an optimal period of time, for example 2 years, and either bioabsorb or break apart and be passed naturally. This may allow the patient to return to his or her natural anatomy after a desired period of time.

The device 2 may include a plurality of weakened regions 32. A weakened region 32 may include a row of openings (e.g., perforations, fenestrations) that extends around an entire circumference of the device 2. In another example, the row of openings may extend around a portion of the circumference of the device 2. The device 2 may include six weakened regions 32—one between the anchor 4 and the sleeve 6 and five between adjacent sections of the sleeve 6. As shown in FIG. 2, the weakened regions 32 may divide the sleeve 6 into six sections. However, the device 2 may include any number of weakened regions 32 dividing the sleeve 6 into any number of sections.

The weakened regions 32 may permit removal of the device 2, section by section, if desired. Because of the radially-outward force exerted by the device 2, tissue ingrowth may make removal of the full intact device difficult. However, to remove a device 2 having weakened regions 32, a surgeon can collapse the anchor 4 in a radially inward direction; rotate the anchor 4, relative to the sleeve 6, around a longitudinal axis of the device 2; and pull the anchor 4 proximally to detach the anchor 4 from the sleeve 6 along the most proximal weakened region 32. The surgeon can use a similar procedure to remove sections of the sleeve 6, beginning by separating the most proximal section of the sleeve 6 from its adjacent distal section along a weakened region 32. In this manner, the device 2 may be removed from the patient, even if tissue ingrowth has secured the device 2 to the intestinal wall. In one example, connectors 28 of frame 22 do not extend across the weakened regions 32.

Still referring to FIG. 2, the membrane 24 of the sleeve 6 may include porous regions 34a-d (referred to generally herein as porous regions 34). Porous regions 34 may include a material that is more permeable than adjacent portions of the sleeve 6, such as portions of the sleeve 6 between porous regions 34. For example, the porous regions 34 may include a mesh-like material that includes openings that would allow chyme to pass through the openings and/or allow digestive fluids or hormones to pass through the openings into the sleeve. For purposes of this disclosure, the term "pore" will be used to refer to an opening in the sleeve 6 and may include micro-pores. The portions of the sleeve adjacent or between the porous regions 34 may be impermeable, or may be permeable to a lesser degree than the porous regions 34. Additionally or alternatively, the porous regions 34 may include openings formed by removing material from membrane 24 (e.g., laser cut openings).

Figure 3:
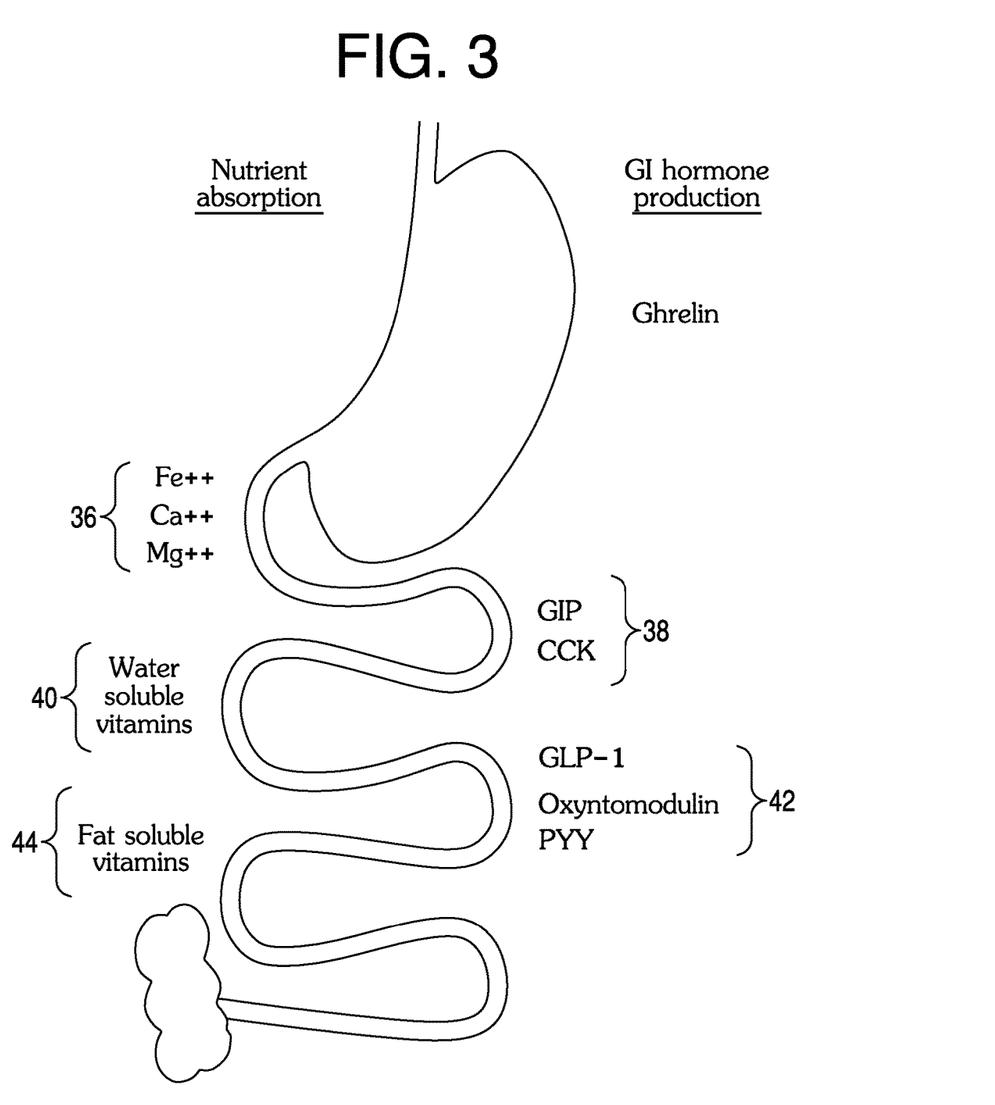
FIG. 3 is a diagram of an intestine showing locations where certain nutrients are absorbed and locations where certain hormones are produced.

Referring to FIG. 3, in various examples, porous regions 34 may align with one or more regions of the intestine 12 that either absorb certain nutrients (e.g., Fe++, Ca++, Mg++, water soluble vitamins, or fat soluble vitamins) or produce hormones that aid in digestion (e.g., GIP, CCK, GLP-1, oxyntomodulin, PYY). The porous regions 34 may allow chyme from the interior of the sleeve 6 to exit the sleeve 6 and contact the intestinal wall, where nutrients may be absorbed. The porous regions 34 may additionally allow digestive fluids to enter the sleeve 6 in regions that produce digestive hormones. The digestive hormones may interact with the chyme inside the sleeve 6, making the nutrients available for absorption if the chyme exits the sleeve 6 via a porous region 34. In one example, a porous region 34 may selectively allow certain nutrients to pass through the wall of the sleeve 6.

Figure 4:
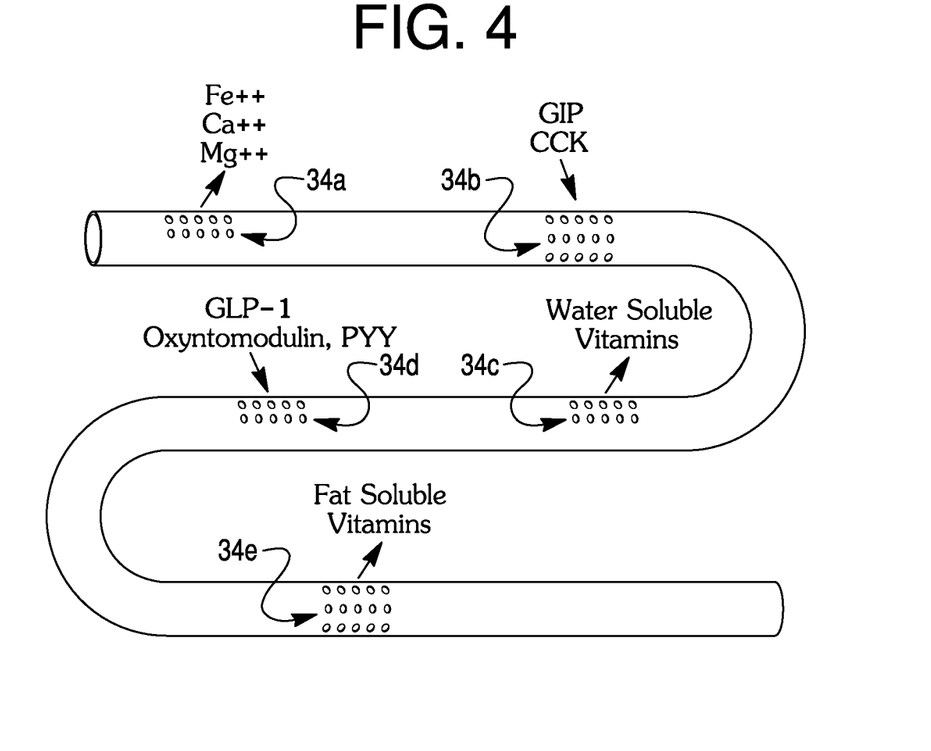
FIG. 4 illustrates several porous regions of a reduced absorption device.

FIG. 4 illustrates a diagrammatic representation of a sleeve 6 with porous regions 34. Porous region 34a may align with region 36 of the intestine, which absorbs Fe++, Ca++, and Mg++; porous region 34b may align with region 38 of the intestine, which produces GIP and CCK; porous region 34c may align with region 40 of the intestine, which absorbs water soluble vitamins; porous region 34d may align with region 42 of the intestine, which produces GLP-1, oxyntomodulin, and PYY; and porous region 34e of the sleeve may align with region 44 of the intestine, which absorbs fat soluble vitamins. Within the intestine, region 38 may be distal to region 36, region 40 may distal to region 38, region 42 may be distal to region 40, and region 44 may be distal to region 42. The portion of sleeve 6 that aligns with a region of the intestine that absorbs fats and carbohydrates may be either impermeable or less permeable than porous regions 34.

Sleeves 6 having variable lengths may be manufactured to appropriately fit the intestines of different patients so that the appropriate sleeve sections (e.g., porous regions 34 or impermeable regions) are adjacent desired regions of the patient's intestine for desired absorption of nutrients and/or entrance of digestive fluids/hormones into the sleeve 6. For example, to optimize nutrient absorption and/or entrance of digestive fluids/hormones, a sleeve 6 for a patient having a shorter intestinal length may include porous regions 34 that are closer together, and a sleeve 6 for a patient having a longer intestine may include porous regions 34 that are farther apart.

Porous regions 34 may differ from each other in a variety of ways, including the total number of pores, the size of individual pores, and the arrangement of pores. Each of these variables may influence nutrient absorption and/or entrance of digestive fluids or hormones into sleeve 6, and a sleeve 6 may include porous regions 34 that include a total number, size, and arrangement of pores configured to optimize nutrient absorption in a particular region. The pores of the device may range in size from very small, for example micro-pores, to relatively large, such as about 10 mm in diameter. In one example, the pore size may be between 1-5 mm in diameter, which may allow tissue ingrowth. The pores may be circular or any other shape, including oval, square, rectangular, or irregularly-shaped. The pore size, density, and region length may vary based on the weight loss goal of the patient and his/her physician. The pore design may be selected based on how much chyme is desired to contact the small intestine inner lumen and hence nutrition uptake from the chyme. For example, a patient with significant comorbidities and wishing to lose significant weight, in agreement with his/her physician, may select a device with low porosity to achieve significant weight loss. An overweight patient with limited comorbidities, in agreement with his/her physician, may select a device with medium porosity, while a more healthy patient, for example just within the obesity category, may choose to select a device with a relatively high porosity. In one example, approximately the first 30 cm of the device 2 may be impermeable, with the mid and distal regions of the device accommodating the porosity, as the duodenum and/or upper small intestine may be regions where carbohydrates tend to be more readily absorbed.

Referring back to FIG. 2, porous region 34a may include a greater number of pores than porous region 34b, and porous region 34c may include a greater number of pores than porous region 34a. Furthermore, some porous regions 34 may include very small micro-openings, while other porous regions 34 may include openings visible to the naked eye. The pores of each porous region 34 may extend around the sleeve 66 to form an ellipse. Although the porous regions 34 in FIG. 2 are illustrated as arranged in an ellipsoidal fashion, the pores of porous regions 34 may be arranged in any configuration. In one example, the pores of two or more porous regions 34 may be arranged in a continuous helical fashion, with at least one variable (e.g., density, size of pores, etc.) being different between different porous regions. In an alternative example, as shown in FIG. 4, the pores of porous regions 34 may be arranged in a series of longitudinal rows and circumferential columns. In other examples, the pores may be arranged in an irregular pattern.

Figure 5:
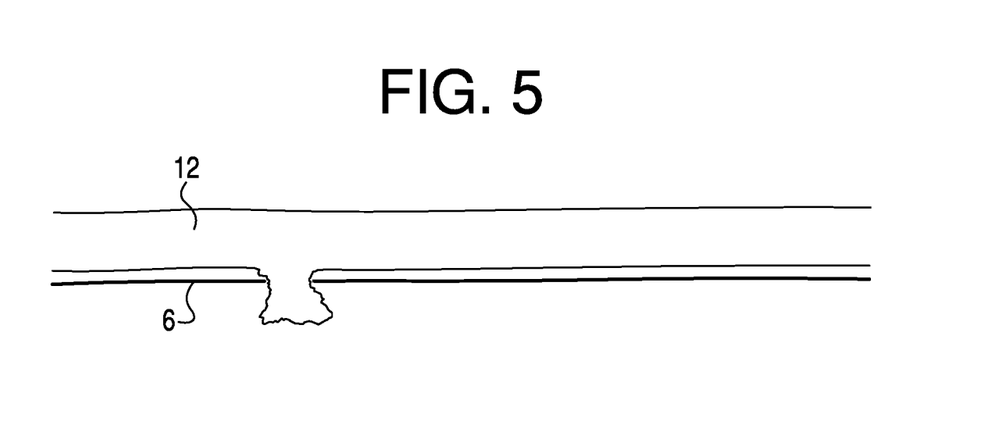
FIG. 5 illustrates an exploded view of a single pore of a reduced absorption device after tissue ingrowth.

Referring to FIG. 5, the pores in a porous region 34 may be large enough to allow tissue of intestine 12 to grow into an interior of sleeve 6. Tissue ingrowth may help secure the device 2 to the patient's intestine. Furthermore, the ingrown tissue may absorb nutrients from the chyme within the sleeve 6 and/or release digestive fluids/hormones into the sleeve 6.

In an additional or alternative example, the material of sleeve 6 may be made of a low-friction material, or the interior of the sleeve 6 may be coated with a low-friction material, relative to the material of the sleeve, to promote faster passage of chyme through the sleeve 6. In another example, the material of sleeve 6 may be made of a high-friction material, or the interior may be coated with a high-friction material relative to the sleeve, to slow the passage of chyme.

Figure 6:
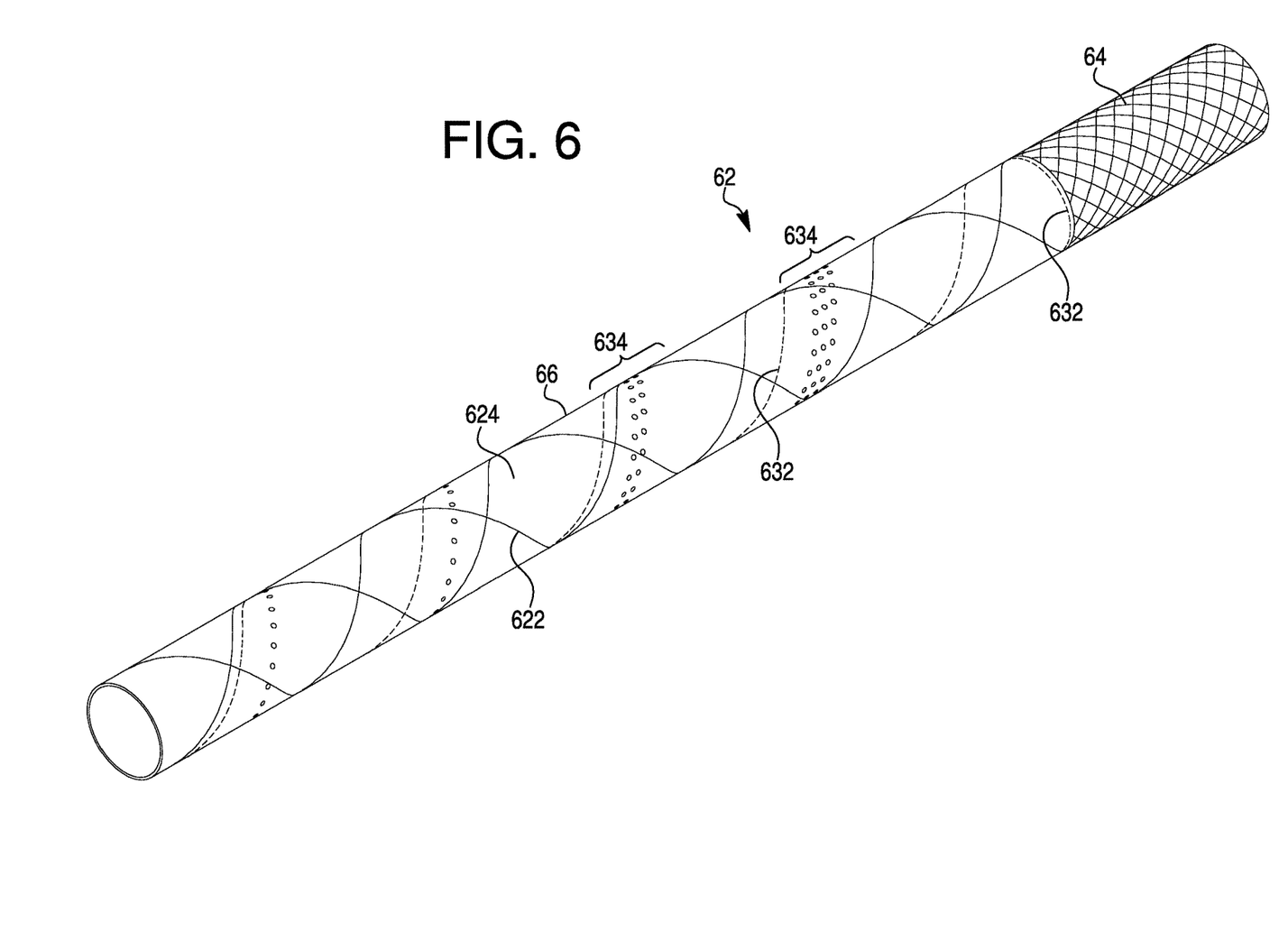
FIG. 6 illustrates a bioabsorbable reduced absorption device.

Referring to FIG. 6, in an additional or alternative example, all or a portion of a reduced absorption device 62 may be bioabsorbable. As used herein, the term bioabsorbable means any material that will degrade over time in the body and includes biodegradable and bioresorbable materials. The device 62 of FIG. 6 may include any of the features described herein in connection with any other example. For example, the device 62 of FIG. 6 may include any of the materials mentioned in connection with FIGS. 1-5, and the device 62 may have porous regions 634 having similar characteristics as the porous regions described above in connection with FIGS. 2-5. In one example, the pores of each porous region 634 may extend around the sleeve 66 to form an ellipse, and the porous regions 634 may be separated from an adjacent porous region by an impermeable region. Alternatively, the pores of one or more porous regions 634 may be arranged in a continuous helical fashion, with at least one variable (e.g., density, size of pores, etc.) being different between different porous regions.

In the example of FIG. 6, the anchor 64 may include a bare braided bioabsorbable frame (e.g., stent). The bare frame may allow tissue ingrowth to help secure the anchor 4 to the intestinal wall. The sleeve 66 may include a braided bioabsorbable frame 622 with a bioabsorbable membrane 624 (e.g., a coated stent). The bioabsorbable membrane 624 may be any bioabsorbable material, such as a bioabsorbable polymer. The anchor 64 may have higher filament count than the frame 622 of the sleeve 6, such that the anchor 64 exerts a larger radially outward force than the sleeve 66 when the device 62 is implanted in the patient.

The components of the device 62 of FIG. 6 may be designed to degrade after a period of time, for example, around six months, one year, two years, or three years. However, if desired, a surgeon may remove the device 62 using one or more weakened regions 632. A first proximal weakened region 632 may separate the anchor 64 and the sleeve 66. A second weakened region 632 may be continuous and may wrap around the sleeve 66 in a spiraled configuration. Once the surgeon removes the anchor 64 from the sleeve 66, the surgeon may collapse the proximal portion of sleeve 66 in a radially inward direction and may pull sleeve 66 proximally to remove the proximal portion from the intestinal wall. With enough force, the sleeve 66 may separate along a proximal portion of the spiraled weakened region 632. The surgeon can then continue to pull successive portions of the sleeve 6 from the intestinal wall, causing the sleeve 66 to progressively separate along spiraled weakened region 632, forming a loose ribbon.

In an additional or alternative example, a device may include an anchor and a sleeve that are modular and configured to be separately implanted in or removed from a patient. The anchor and sleeve may include a connection feature that allows the proximal end of the sleeve to removably connect to the distal end of the anchor. For example, the anchor may include hooks, and the sleeve may include openings or loops. The anchor and sleeve may be connected prior to implantation of the components. Alternatively, one of the anchor or sleeve may be implanted first, and the other component may be implanted afterwards and coupled to the previously-implanted component. In one example, to end a reduced absorption treatment, the sleeve may be decoupled from the anchor and removed from the patient while the anchor remains within the patient. Such a feature may allow the sleeve to be replaced at a later date with a new sleeve, if necessary. It may be desired for patient treatment to replace the sleeve with a new sleeve having different porous regions.

The various devices described herein may be implanted into a patient's intestine transorally and through the esophagus and stomach, and an endoscope may be used to visualize placement. Both the proximal and distal ends of the device may be placed in the intestine distal to the pyloric sphincter. The proximal end of the device may be positioned distal to the duodenal papilla, allowing bile and pancreatic fluid to mix with the chyme. Alternatively, the proximal end of the device may be positioned proximal to the duodenal papilla. Positioning the proximal end of the device proximal to the duodenal papilla may cause greater malabsorption effects relative to positioning the proximal end distal to the duodenal papilla because bile and pancreatic fluids may be at least partially prevented from mixing with chyme.

Several features of the reduced absorption device may induce weight loss in a patient by reducing absorption of food, while allowing the body to absorb certain necessary nutrients from food. For example, the sleeve having the porous regions may allow chyme to pass through the sleeve at select locations so that the intestine may absorb nutrients from the chyme. Furthermore, intestinal tissue may grow through the pores and into an interior of the sleeve, where chyme will contact the ingrown tissue. In addition, the material of an inner portion of the sleeve may affect the propulsion of chyme, which may reduce absorption. Placement of the device relative to anatomical features, such as the duodenal papilla, may further affect the absorption of food by limiting or allowing the mixing of chyme with digestive fluids.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A reduced absorption device, comprising:
   a proximal anchor including a plurality of circumferential loops and a plurality of connectors extending between the circumferential loops, wherein the connectors extend radially outward relative to the circumferential loops; and
   a distal sleeve including a frame and a membrane;

wherein the membrane includes a plurality of porous regions, wherein each porous region is configured to align with a corresponding region of an intestine configured to absorb nutrients.

2. The device of claim 1, wherein the membrane includes a plurality of weakened regions, at least one weakened region being configured to allow the anchor to separate from at least a portion of the sleeve.

3. The device of claim 1, wherein the anchor includes a self-expandable frame.

4. The device of claim 1, wherein the anchor includes a plurality of attachments configured to secure the anchor to the intestine.

5. The device of claim 1, wherein the sleeve includes at least three porous regions, wherein a first porous region is configured to align with a first region of the intestine configured to absorb nutrients, a second porous region is configured to align with a second region of the intestine, the second region of the intestine being distal to the first region of the intestine and being configured to absorb water soluble vitamins, and a third porous region is configured to align with a third region of the intestine, the third region of the intestine being distal to the second region of the intestine and being configured to absorb fat soluble vitamins.

6. The device of claim 1, wherein the sleeve includes at least five porous regions, wherein a first porous region is configured to align with a first region of the intestine that absorbs Fe++, Ca++, and Mg++, a second porous region is configured to align with second region of the intestine that produces GIP and CCK, a third porous region is configured to align with third region of the intestine that absorbs water soluble vitamins, a fourth porous region is configured to align with a fourth region of the intestine that produces GLP-1, oxyntomodulin, and PYY, and a fifth porous region is configured to align with a fifth region of the intestine that absorbs fat soluble vitamins.

7. The device of claim 1, wherein each porous region is separated from an adjacent porous region by an impermeable region.

8. The device of claim 1, wherein at least one porous region differs from at least one other porous region by at least one of a) total number of pores, b) the size of individual pores, or c) the arrangement of pores.

9. The device of claim 1, wherein the distal sleeve is self-expandable.

10. The device of claim 1, wherein an interior of the sleeve is coated with a material that is a lower friction material than a material of the sleeve.

11. A reduced absorption device, comprising:
a proximal bioabsorbable frame; and
a distal sleeve including a sleeve bioabsorbable frame and a bioabsorbable membrane, wherein the membrane includes a plurality of porous regions, each porous region being separated from an adjacent porous region by an impermeable region, wherein the sleeve includes a weakened region in a spiral configuration around the sleeve, and wherein the sleeve is configured to separate along the weakened region.

12. The device of claim 11, wherein the proximal bioabsorbable frame and the sleeve are modular components configured to be at least one of separately implanted in the patient or separately removed from the patient.

13. A method for reducing absorption in a patient, comprising:
positioning a reduced absorption device within an intestine of the patient, the reduced absorption device including a proximal anchor and a distal sleeve, wherein the proximal anchor is positioned distal to a pyloric sphincter, wherein the sleeve includes a frame and a membrane, and wherein the membrane includes a plurality of porous regions; and
aligning a first porous region of the sleeve with a first region of the intestine configured to absorb nutrients, aligning a second porous region of the sleeve with a second region of the intestine, the second region of the intestine being distal to the first region of the intestine and being configured to absorb water soluble vitamins, and aligning a third porous region of the sleeve with a third region of the intestine, the third region of the intestine being distal to the second region of the intestine and being configured to absorb fat soluble vitamins.

14. The method of claim 13, wherein the distal sleeve is self-expandable.

15. The method of claim 13, wherein positioning the reduced absorption device includes transorally introducing the device and passing the device through an esophagus and a stomach.

16. The method of claim 13, further comprising aligning at least one porous region of the membrane with a region of the intestine configured to produce digestive hormones.

17. The method of claim 13, wherein positioning the reduced absorption device includes positioning the anchor proximal to the duodenal papilla.

* * * * *